(12) United States Patent
Lee et al.

(10) Patent No.: US 9,375,531 B2
(45) Date of Patent: Jun. 28, 2016

(54) SYRINGE PUMP WITH IMPROVED FLOW MONITORING

(71) Applicant: Zyno Medical LLC, Natick, MA (US)

(72) Inventors: Chaoyoung Lee, Weston, MA (US); Mei Zhang, Sharon, MA (US); Cunyou Lu, Framingham, MA (US)

(73) Assignee: Zyno Medical, LLC, Natick, MA (US)

( * ) Notice: Subject to any disclaimer, the term of this patent is extended or adjusted under 35 U.S.C. 154(b) by 0 days.

(21) Appl. No.: 13/659,619

(22) Filed: Oct. 24, 2012

(65) Prior Publication Data

US 2014/0114238 A1 Apr. 24, 2014
US 2016/0175519 A9 Jun. 23, 2016

Related U.S. Application Data

(60) Provisional application No. 61/552,300, filed on Oct. 27, 2011.

(51) Int. Cl.
*A61M 5/168* (2006.01)
*A61M 5/172* (2006.01)
*A61M 5/145* (2006.01)

(52) U.S. Cl.
CPC ......... *A61M 5/16877* (2013.01); *A61M 5/1456* (2013.01); *A61M 5/16804* (2013.01); *A61M 5/16831* (2013.01); *A61M 5/16854* (2013.01); *A61M 5/172* (2013.01)

(58) Field of Classification Search
CPC .............. A61M 5/172; A61M 5/1723; A61M 2005/1726; A61M 5/168; A61M 5/16831; A61M 5/16854; A61M 2005/14573; A61M 5/16886; A61M 5/16877; G01F 1/667
USPC ...................... 604/65–67, 154, 131
See application file for complete search history.

(56) References Cited

U.S. PATENT DOCUMENTS

| | | | |
|---|---|---|---|
| 4,776,837 A * | 10/1988 | Kopp | 604/6.05 |
| 5,178,153 A * | 1/1993 | Einzig | 600/505 |
| 5,533,412 A * | 7/1996 | Jerman et al. | 73/861.95 |
| 6,164,921 A * | 12/2000 | Moubayed et al. | 417/44.1 |
| 6,673,033 B1 | 1/2004 | Sciulli et al. | |
| 6,939,302 B2 * | 9/2005 | Griffiths et al. | 600/458 |
| 7,753,885 B2 | 7/2010 | Duchon et al. | |
| 8,147,479 B1 * | 4/2012 | Wach et al. | 604/522 |
| 8,182,461 B2 | 5/2012 | Pope et al. | |
| 2003/0159741 A1 * | 8/2003 | Sparks | 137/814 |
| 2003/0171712 A1 * | 9/2003 | Critchlow et al. | 604/67 |
| 2003/0236489 A1 * | 12/2003 | Jacobson et al. | 604/67 |
| 2004/0171983 A1 * | 9/2004 | Sparks et al. | 604/65 |
| 2009/0138215 A1 * | 5/2009 | Wang et al. | 702/48 |
| 2010/0211003 A1 * | 8/2010 | Sundar | A61M 5/16813 604/67 |
| 2010/0274216 A1 * | 10/2010 | Wade | 604/500 |

* cited by examiner

*Primary Examiner* — Theodore Stigell
*Assistant Examiner* — Benjamin Koo
(74) *Attorney, Agent, or Firm* — Boyle Fredrickson, S.C.

(57) ABSTRACT

A syringe pump provides a controlled metering of the medicament from a syringe by movement of the syringe plunger while also measuring flow from the syringe with a flow sensor. Simultaneous monitoring of flow command implicit in control of the syringe plunger and an actual flow provides additional safety and detection of irregularities in the delivery of the medicament.

10 Claims, 4 Drawing Sheets

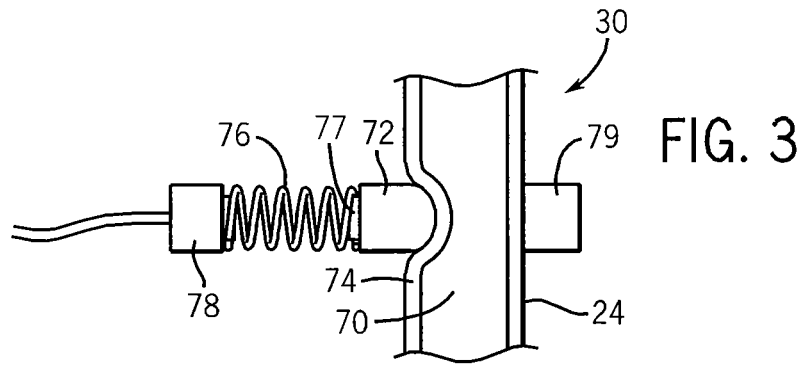
FIG. 3
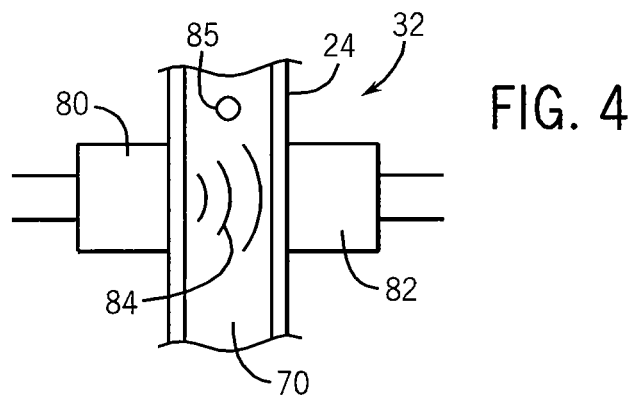
FIG. 4
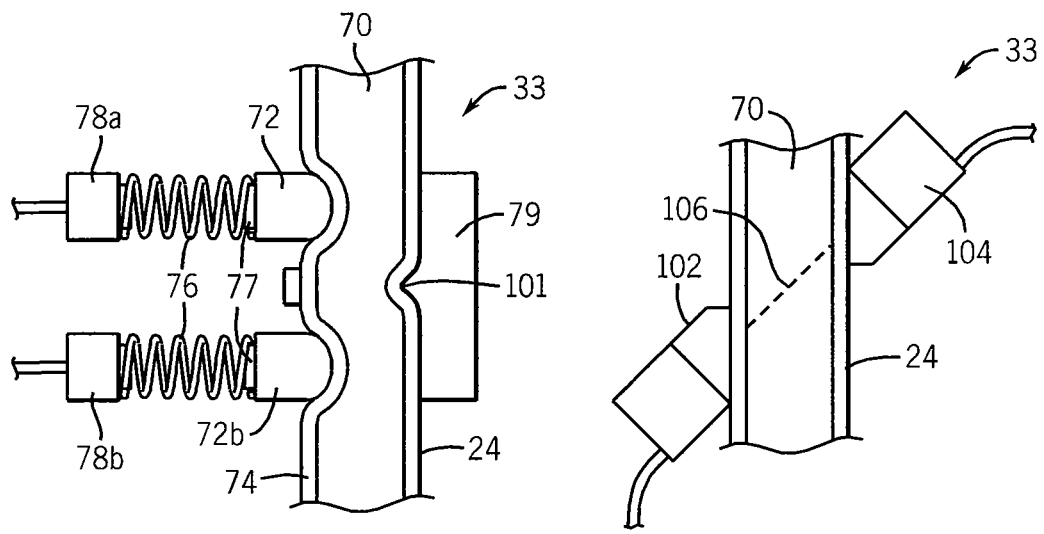
FIG. 5
FIG. 6

SYRINGE PUMP WITH IMPROVED FLOW MONITORING

CROSS REFERENCE TO RELATED APPLICATION

This application claims the benefit of U.S. provisional application 61/552,300 filed Oct. 27, 2011 and hereby incorporated by reference in its entirety.

BACKGROUND OF THE INVENTION

The present invention relates to syringe pumps as used for medical purposes and in particular to a syringe pump that provides improved monitoring of its operation.

Syringe pumps are known for use to administer certain amounts of fluid, for example medication or contrast agents (henceforth medicaments), to a patient over a period of time. Such pumps use a syringe comprised of a plunger sliding in a syringe tube. The plunger includes a piston-like seal that fits tightly against the inner surface of the syringe tube. Movement of the plunger decreases the volume contained in the syringe tube between the plunger seal and an outlet of the syringe tube to provide a positive displacement pumping action.

The syringe pump includes a syringe driver which provides movement of the plunger with respect to the tube via an electric motor. The motor can provide precise and slow movement of the plunger to deliver intravenous medications over several minutes without the need for a human operator. Flow rate may be controlled by knowing the geometry of the syringe and accurately controlling movement of the plunger.

The syringe pump may be connected to the patient by a standard intravenous (IV) line terminated with a hypodermic needle or the like.

SUMMARY OF THE INVENTION

The present invention provides a syringe pump with improved flow rate monitoring that may be used to detect problems with the IV line or its connection to the patient downstream from the syringe. Monitoring the flow rate deduced independently of known motion of the syringe, allows problems with obstructed flow or disconnection of the IV line to be determined. Monitoring the flow rate as well as other flow conditions such as air bubble in flow and pressure is made practical by use of sensors on the downstream tubing. Flow monitoring can be performed from outside the IV line to preserve the sterile environment of the IV line or may be integrated into the IV line in a pre-sterilized unit.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

BRIEF DESCRIPTION OF THE FIGURES

FIG. 3 is a simplified cross-sectional representation of a through-tubing pressure sensor suitable for use with the present invention;

FIG. 4 is a simplified cross-sectional representation of a through-tubing air bubble sensor suitable for use with the present invention;

FIG. 5 is a simplified cross-sectional representation of a through-tubing flow rate monitor employing two pressure sensors of the type shown in FIG. 3;

FIG. 6 is a simplified cross-sectional representation of a through-tube flow rate monitor employing ultrasound;

DETAILED DESCRIPTION OF THE PREFERRED EMBODIMENT

Figure 1:
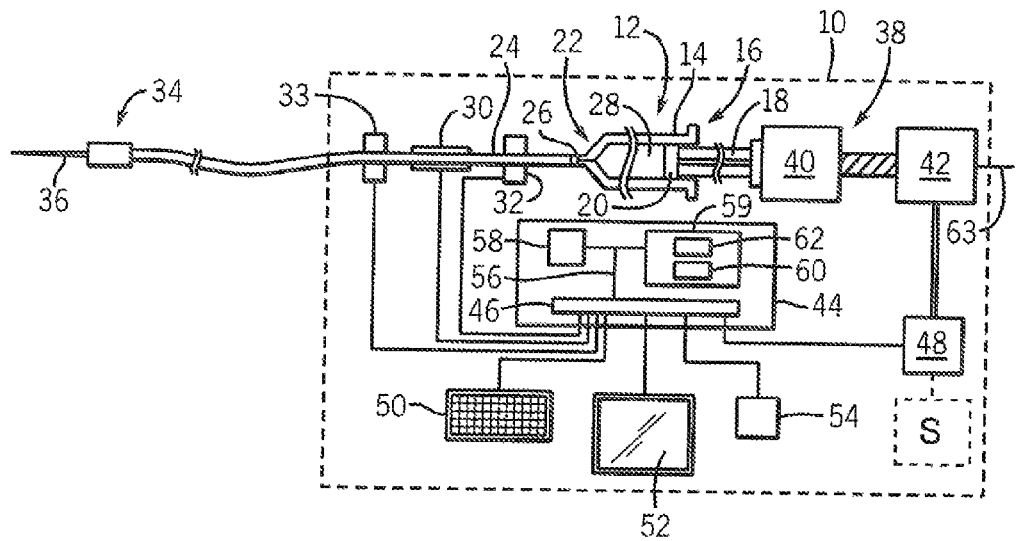
FIG. 1 is a block diagram of a syringe pump according to the present invention and showing a syringe and a syringe driver, the latter communicating with a control computer also receiving signals from downstream IV line sensors.

Referring now to FIG. 1, a syringe pump 10 of the present invention may employ a syringe 12 similar to a typical hypodermic syringe and having a syringe tube 14 with a first open end 16 receiving a plunger 18. One end of the plunger 18 within the syringe tube 14 is connected to a piston seal 20 (for example of an elastomeric material) fitting snugly within the volume of the syringe tube 14.

A second end 22 of the syringe tube 14, opposite the open end 16, connects to an IV tubing 24, for example by a luer connector 26 or the like, to provide a continuous passageway between a hypodermic volume 28 contained between the piston seal 20 and the luer connector 26 of the IV tubing 24.

The IV tubing 24 may be a highly compliant material that may be sterilizable and is, preferably, non-Pyrogenic, non-DEHP and Latex free. One such material is silicone rubber which provides for high compliance as will be desired for pressure sensing to be described below. Another example is Non-DEHP PVC material. The IV tubing 24 passes from the syringe 12 through a bubble sensor 32, a pressure sensor 30 and a flow sensor 33 and may be installed in bubble sensor 32, the pressure sensor 30 and flow sensor 33 by being pressed into a gap between opposing walls of each of the bubble sensor 32 and flow sensor 33 and pressed against the pressure sensor 30 by a backstop 79 on a cover 68 to be described below. The IV tubing 24 may then proceed to a patient-end 34 where it attaches to a hypodermic needle 36, catheter or other patient connection.

A portion of the plunger 18 extending away from the piston seal 20 and out of the syringe tube may be connected to a syringe driver 38. The syringe driver 38 includes a plunger block 40 constrained for linear movement along an axis of the syringe tube 14 as driven by a motor 42. The motor 42 may be, for example, a stepper motor or servomotor or the like and include an appropriate mechanism for speed reduction and conversion of rotary to linear motion, such as may be implemented by a linear screw, rack and pinion, belt drive or the like. The motor 42 receives power from a motor controller 48 to provide movement of the plunger block 40 to move the piston seal 20 through the volume of the syringe tube 14 at a controlled rate and controlled distance. Various position or velocity sensors such as encoders, tachometers, limit switches, and the like may be used to communicate with the motor controller 48 as is understood in the art to provide such controlled motion. In addition, the sensors can provide a first estimate of a flow of medicament from the syringe based on known dimensions of the syringe tube 14.

An electronic controller 44 may coordinate operation of the syringe pump 10 through interface circuitry 46 of a type known in the art communicating with motor controller 48, the pressure sensor 30, the air bubble sensor 32, and flow sensor 33. In addition, the interface circuitry 46 may receive signals from a keypad 50 allowing for user entry of data or commands. In addition, the interface circuitry 46 may output data to a display 52 (for example a liquid crystal type alphanumeric and/or graphic display) and/or speaker 54.

Generally, the interface circuitry 46 will communicate via an internal bus structure 56 with a processor 58. The processor 58 may read data 60, for example, entered by the user through the keypad 50 or stored in an electronic memory 59 and may execute a stored program 62 (also stored in the electronic memory 59) to provide data to the display 52 according to conventionally known techniques.

Figure 2:
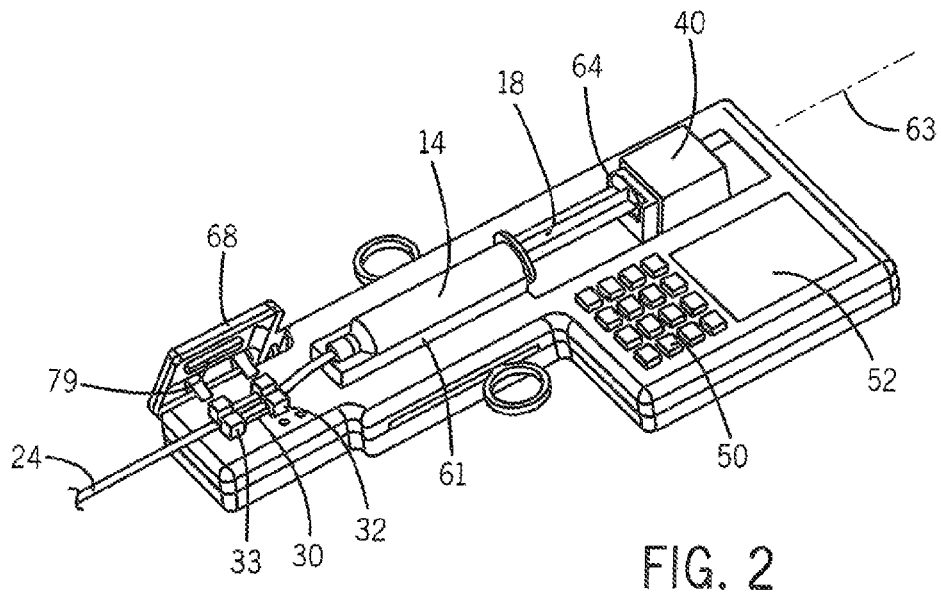
FIG. 2 is a simplified perspective view of one embodiment of the syringe driver of the present invention showing lateral engagement of the IV line with the downstream sensors by pressing the IV line into a channel.

Referring now to FIG. 2, the syringe pump 10 may provide, for example, a housing supporting the various components described above and including a cradle 61 receiving the body of the syringe tube 14. The cradle 61 provides a generally upwardly open channel to receive the syringe tube 14 in a direction perpendicular to an axis 63 of the syringe tube 14 to allow a newly charged syringe tube 14 to be easily installed in the syringe pump 10.

The plunger block 40 may similarly provide an upwardly open slot 64 engaging an external portion of the plunger 18 to hold the plunger 18 to the plunger block 40, so that the plunger 18 moves with the plunger block 40. The IV tubing 24 may be pre-attached to the syringe tube 14 and pass through a notch in the cradle 61 to be received by upstanding flanking walls of the bubble sensor 32 and flow sensor 33 and over the pressure sensor 30 before exiting from the housing to pass to the patient. A cover 68 may fit over the bubble sensor 32, the pressure sensor 30 and the flow sensor 33 to shield them from an external interference and to locate and properly retain the IV tubing 24 in the bubble sensor 32, pressure sensor 30, and flow sensor 33 and to provide a backstop 79 for the pressure sensor 30 described below.

Referring now to FIG. 3, the pressure sensor 30 may measure pressure of medicament 70 passing through the IV tubing 24 through the walls 74 of the IV tubing 24 so as to avoid the need for separate connections to the fluid-contacting pressure sensor and to avoid problems of sterilization of a fluid-contacting pressure sensor. In such a through-tubing sensing system, a spring-loaded plunger 72 may deform a portion of a wall 74 of the IV tubing 24 as held against a backstop 79, for example, under a known spring biasing force from a spring 76. An amount of deflection of the wall 74 may be measured, for example, by a Hall Effect sensor 78 positioned at the opposite end of the spring 76 from the plunger 72, the latter which have an attached magnet 77. The Hall Effect sensor can be positioned at other positions as well. This deflection may be corrected for known characteristics of the IV tubing 24. Increased deflection of the wall 74 for a known material of the IV tubing 24 and the known spring biasing force of spring 76 may be converted to a pressure reading based on the proximity of the plunger 72 and magnet 77 with a Hall Effect sensor 78. Generally, lower pressures of the medicament 70 will allow greater deflection of the wall 74 and higher pressures of medicament 70 will allow less deflection of the wall 74. Alternative pressure sensing systems may be used and in this system other sensors other than a Hall effect sensor may be used for position monitoring including photo optic sensors.

Referring now to FIG. 4, the bubble sensor 32 may employ opposed ultrasonic transducers 80 and 82 transmitting an ultrasonic signal 84 through the medicament 70 in the IV tubing 24. The occurrence of a bubble 85 between the transducers 80 and 82 will attenuate the ultrasonic signal passing between the transducers 80 and 82 resulting in a decrease in signal strength at receiving transducer 82 which may be compared to a threshold adjustably set to detect bubbles 85 of a given size.

The flow sensor 33 may employ, for example, the following techniques:
(1) Ultrasonic, for example, through-tubing ultrasonic Doppler or ultrasonic transit time measurement and the supporting circuits.
(2) Infrared, for example, an Infrared (IR) emitter/emitters emitting IR light, IR detector(s), and the supporting circuits.
(3) Turbine and paddle wheel or alike
(4) Laser based flow sensor and the supporting circuits.
(5) Thermal time of flight based flow sensor and the supporting circuits.
(6) Differential pressure based techniques, such as two pressure sensors, or one differential pressure sensor, such as a piezoresistive monolithic silicon pressure sensor.

Referring now to FIG. 5, in one embodiment, the flow sensor 33 may measure the flow of medicament 70 passing through IV tubing 24 by measurements made through two pressure measurements made outside of the walls 74 of the IV tubing (again to avoid the need for separate connections to a fluid-contacting flow sensor and to avoid problems of sterilization of that fluid-contacting pressure sensor). In the manner described above with respect to FIG. 3, an upstream spring-loaded plunger 72a and a downstream spring-loaded plunger 72b may deform axially in separated portions of the wall 74 of the IV tubing 24 as held against a backstop 79 under a known spring biasing force of springs 76. As described before, a deflection of the wall 74 may be measured, for example, by corresponding Hall effect sensors 78a and 78b positioned at opposite ends of the spring 76 from their respective plungers 72 which each may have an attached magnet 77. Signals from Hall effect sensors 78a and 78b are transmitted to the electronic controller 44 and corrected for known characteristics of the IV tubing 24 and difference in pressure between the measurements made by the Hall effect sensor 78a and 78b determined. This pressure difference indicates pressure drop through the IV tubing 24, a parameter that will change as a function of flow and thus may be used to deduce flow. Generally, lower pressure differences will indicate lower flow rates. This effect may be accentuated by a slight constriction in the IV tubing 24 between the pressure sensors, the latter provided, for example, by a protrusion 101 from the backstop 79 constricting the flow in between the pressure sensors. It will be understood that other methods of determining flexure of the IV tubing may be used including capacitive or optical sensing.

Referring now to FIG. 6, in an alternative flow sensing arrangement that does not breach the sterile envelope of the IV tubing 24, an ultrasonic transmitter 102 may be positioned across the IV tubing 24 from an ultrasonic receiver 104 to provide a path of ultrasonic transmission 106 through the medicament 70 extending at least partly along the axis of the IV tubing 24. Changes in the ultrasonic transmission between the ultrasonic transmitter 102 and ultrasonic receiver 104, such as transmission delay or Doppler shift in frequency can then be processed by the electronic controller 44 and used to deduce flow rate of the medicament 70.

Figures 7, 8:
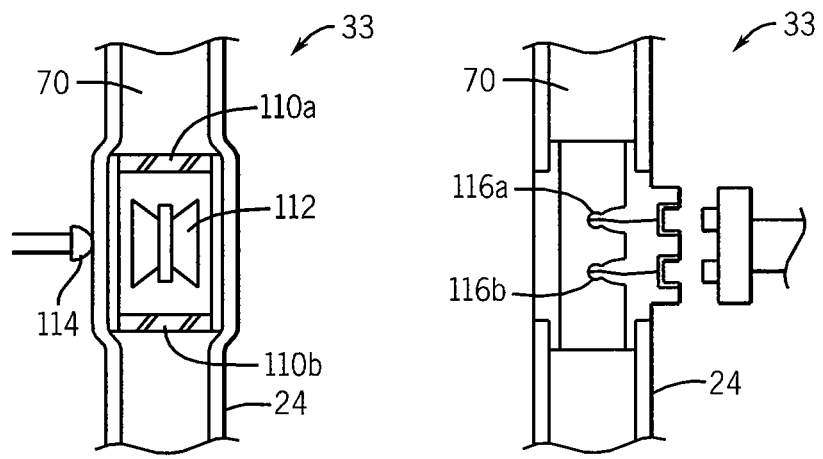
FIG. 7 is a simplified cross-sectional view of an integrated in-tube flow sensor employing a rotating mechanical element.
FIG. 8 is a simplified cross-sectional view of an integrated in-tube flow sensor employing heating and thermal sensing elements.

Referring now to FIG. 7, an alternative flow sensor 33 may be integrated into an IV tubing 24, for example by ultrasonic welding of the tubing 24 and components of the flow sensor 33 together, and sterilized before use to address the problems of direct contact between the medicament 70 and the sensor structure. In particular, the sensor structure may include axially aligned inlet and outlet flow formers 110a and 110b, respectively, which generate a controlled axial swirl in the medicament 70. In between the flow formers 110 may be free-turning vane assembly 112 (wheel turbine) whose speed of rotation will depend on the flow of the medicament through the IV tubing 24. This speed may be deduced externally by a sensor 114 such as an optical sensor, a variable reluctance sensor, a Hall effect sensor (assuming a magnet on the vane assembly 112) or a capacitive sensor or the like, sensing changes in these parameters with rotation of the vane assembly 112. This design may alternatively eliminate the flow formers in favor of a helix shaped vane assembly 112.

Referring now to FIG. 8, an alternative flow sensor 33 may also be built into the IV tubing 24 to be sterilized with the IV tubing 24 as a unit and provides axially separated first and second thermal sensors 116a and 116b having electrical leads passing hermetically through a wall of the IV tubing 24 to be received by one half of a connector shell that allows releasable electrical connection to the electronic controller 44. One of the thermal sensors, for example thermal sensor 116a, may be heated by a slight electrical current and a difference between temperatures of the thermal sensors 116a and 116b used to deduce flow rate according to known techniques.

Figure 9:
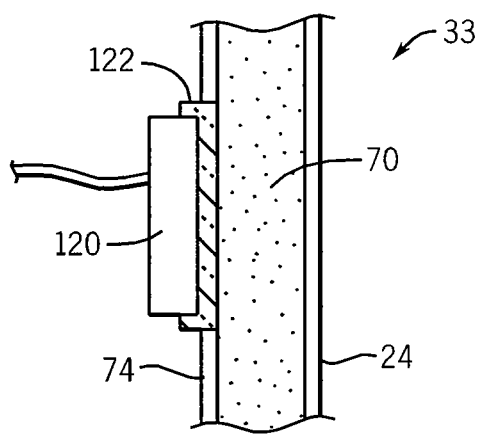
FIG. 9 is a simplified cross-sectional representation of a through-tube flow rate monitor employing optical sensing elements.

Referring now to FIG. 9, an optical flow sensor 33 may provide an optical sensor array 120 that can optically interrogate the medicament 70 as it passes by the optical flow sensor 33. This optical sensor array 120 may detect a moving pattern of minor optical inclusions in the medicament 70 in the manner of an optical mouse to deduce linear speed of the medicament and hence volume flow based on the known diameter of the IV tubing 24. LED or laser technologies may be used for this purpose together with an array of photo detectors or CCD linear camera. This particular sensor may work through the wall 74 of the IV tubing 24 or, for improved accuracy, may be integrated into the IV tubing 24, or may interface with an optical window 122 integrated into the IV tube 24 as shown. Example circuitry for implementing this optical array is taught generally in U.S. Pat. No. 6,664,948 hereby incorporated by reference as may be modified to the use of a backlight or front lighting system for this purpose.

Figure 10:
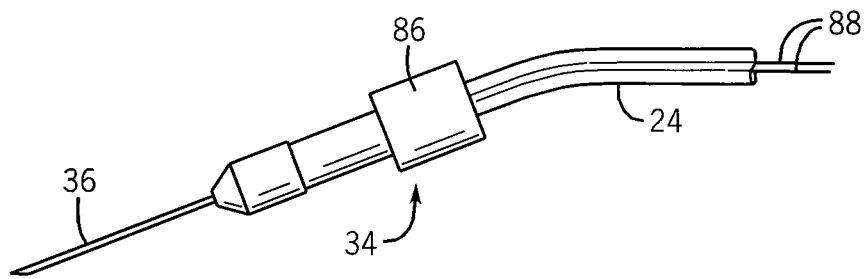
FIG. 10 is a fragmentary view of the needle-end of the IV tubing showing an alternative embodiment employing a remotely located pressure sensor.

Referring now to FIG. 10, in one embodiment, the patient-end 34 of the IV tubing 24 may alternatively or also provide a sensor positioned on the IV tubing 24 close to the patient. In this implementation, the sensor 86 may measure not only the changing pressure of the medicament 70 but may also measure, or alternatively measure, fluctuations in IV tubing or its connector caused by coupling of the medicament 70 to the vascular system as transmits pressure fluctuations caused by beating of the patient's heart through the liquid 75 to the sensor 86. The sensor 86 may be similar to the pressure sensor 30 using a plunger technique, or may use a piezoelectric transducer or MEMS-type accelerometer or the like. Other pressure sensing techniques may also be used. Signals from the sensor 86 may be transmitted through thin wires 88 running along the outside of the IV tubing 24, or embedded in the IV set tubing wall, or may be transmitted wirelessly or the like.

Figure 11:
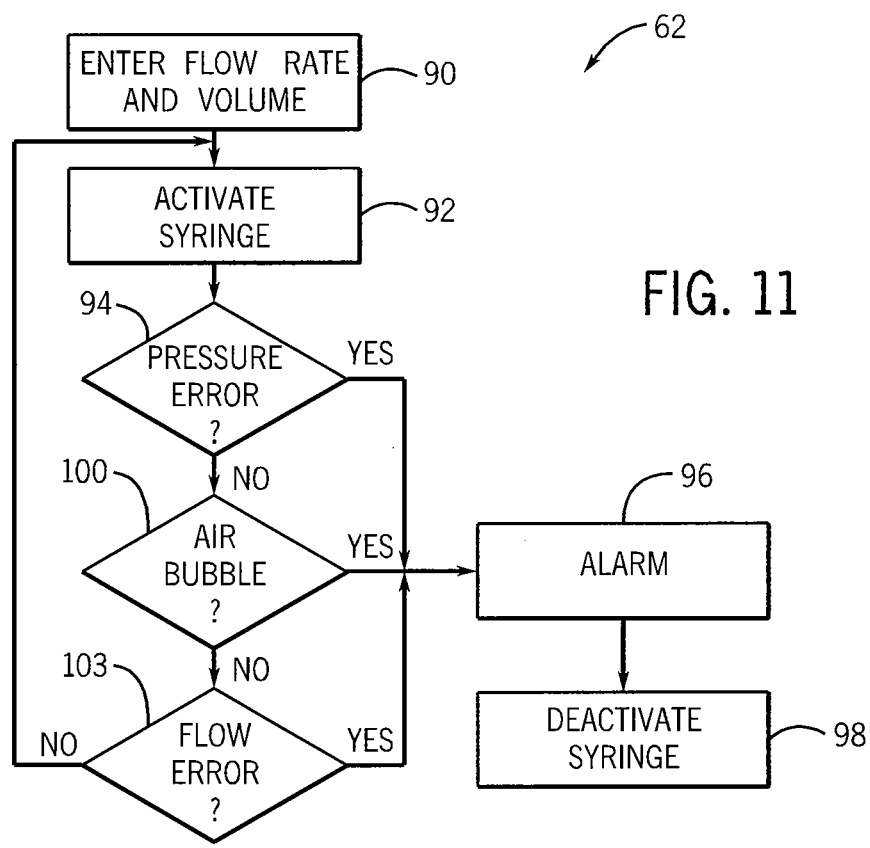
FIG. 11 is a flow chart of a program executable by the controller of FIG. 1 for monitoring the operation of the syringe pump.

Referring now to FIGS. 1 and 11, program 62 may make use of information from the pressure sensors 30 and/or 86 to detect problems with the delivery of medicament 70 to a patient by the syringe pump 10 that would normally be difficult to detect based on the slow flow rates of the delivery of liquid 75 by the syringe pump 10. Generally, problems with flow are deduced by changes in IV line pressure. For example, pressure increases above a certain amount detected by pressure sensor 30 may indicate an occlusion of the IV tubing 24 that requires attention. Conversely, pressure drops below a certain amount may indicate that the IV tubing 24 has become disconnected or broken. With respect to pressure sensor 86, alternative information that may indicate disconnection of the IV tubing 24 can be derived from a loss of the dynamic heartbeat pressure signal that may be detected by the sensor 86.

Generally, the operation of the program 62 will allow data entry through the keypad 50 by a user as confirmed through display 52. This data may include a desired flow rate and volume of medicament 70 for delivery from the syringe tube 14. This data entry process is indicated by process block 90. At succeeding process block 92, typically after an activation command by a user at process block 90, the motor 42 will be activated to produce the desired flow rate and volume per process block 92.

At decision block 100, the air bubble sensor 32 may be interrogated to see whether there is an air bubble in the IV tubing 24. If so, the program proceeds to process block 98 to provide the alarm and disabling of further delivery of medicament 70.

If there is no air bubble, at decision block 94, pressure sensor 30 and/or 86 are checked to determine whether there has been a pressure deviation indicating either disconnection, breakage or obstruction of the IV tubing 24. If such problems are detected, the program 62 proceeds to process block 95 to correct the motor drive in a closed loop fashion to bring the pressure into proper range. If that correction is not successful as indicated by decision block 96 program proceeds to process block 98 to deactivate the pump and set an alarm. Generally the alarm may be, for example, a tone or spoken warning provided through speaker 54, the latter provided by speech synthesis techniques well known in the art. The alarm may be accompanied or followed immediately by deactivation of the syringe pump 10 per process block 98, ceasing delivery of medicament 70.

If there is no pressure deviation detected at decision block 94, then the program proceeds to decision block 103 where the flow sensor 33 is interrogated to see whether proper flow rates are being provided. A determination of proper flow rates may compare the deduced flow rate from the flow sensor 33 against a range normalized to operation of the motor controller 48. Generally the range is a small band around zero flow when the motor controller 48 is not operating and changes to a small band around a calculated flow based on operation of the motor controller 48 and a geometry of the syringe tube 14 when the motor controller 48 is activated to move the motor 42. A flow higher than this range may indicate that the IV tube has become disconnected from the patient. In this situation, the motor 48 will be running at a faster rate than it should but an internal calculation from the motor speed may have error (for example, because a smaller syringe diameter may have been used in the calculation than the actual syringe diameter); etc. A flow lower than this rate may indicate an obstruction downstream from the syringe tube 14. In this situation, the motor will be running at a slower rate than it should and again the internal calculation from the motor speed alone may have error (for example, because it uses a larger syringe diameter in the calculation than the actual size of the syringe); etc. If the flow rate is within range, the program returns to process block 92 to complete movement of the syringe to the desired volume. Otherwise, the program 62 proceeds to process blocks 95 and 96 as described above for closed loop control to adjust the flow rate by adjusting motor speed, and if this is not successful, possibly to process block 98 to provide the alarm and disabling of further delivery of medicament 70.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A syringe pump comprising:
    a housing adapted to hold a syringe holding a liquid medicament;
    a motor drive attached to the housing having a portion adapted to hold a plunger portion of the syringe to move the plunger portion within a tube portion of the syringe according to a motor drive signal to eject the medicament from the syringe;
    a motor controller powering the motor drive to provide movement of the plunger portion within the tube portion at a controlled rate and a controlled distance and in communication with one or more sensors to provide a flow estimate of medicament from the syringe based on known dimensions of the syringe tube and operation of the motor controller;
    a flow sensor adjacent to a flow of medicament from the syringe and adapted to measure the flow of the medicament through a downstream elastomeric IV tube in communication with the syringe; and
    an electronic controller configured to (i) interrogate the flow sensor to determine the flow of medicament, (ii) determine an acceptable flow range around zero when the motor controller is not operating and around the flow estimate when the motor controller is activated, (iii) compare the flow of medicament with the acceptable flow range to detect a flow error arising from a difference between the flow of the medicament and the acceptable flow range, and (iv) deactivate or adjust the motor drive upon detection of the flow error;
    wherein the flow sensor is adapted to releasably receive the elastomeric IV tube passing from the syringe to a patient and having substantially continuous tubing walls unbroken by the flow sensor, the flow sensor positioned entirely outside the tubing walls of the IV tube without piercing the IV tube and without contact with fluid within the IV tube;
    further including a pressure sensor adapted to releasably receive the elastomeric IV tube, the pressure sensor positioned entirely outside the tubing walls of the IV tube without piercing the IV tube and without contact with the fluid within the IV tube indicate a pressure of the medicament within an IV line attached to the syringe and communicate the pressure to the electronic controller.

2. The syringe pump of claim 1 further including an alarm indicator for a user of the syringe pump and wherein the electronic controller activates the alarm upon detection of at least one of the flow error and a pressure error.

3. The syringe pump of claim 2 wherein the flow error is a flow rate outside of the acceptable flow range.

4. The syringe pump of claim 3 wherein the electronic controller provides a pump speed command to the motor drive and wherein the acceptable flow range is a function of pump speed command.

5. The syringe pump of claim 4 wherein the flow sensor deduces flow from pressure differential along a length of the IV tube.

6. The syringe pump of claim 4 wherein the flow sensor includes an ultrasonic transducer and ultrasonic receiver emitting and receiving ultrasonic sound and wherein the second flow sensor deduces flow through a change in ultrasonic transmission speed of the ultrasonic sound through the liquid medicament as measured along an axis of the tube.

7. The syringe pump of claim 4 wherein the flow sensor deduces flow through at least one of a change in tubing deformation or moving pattern of minor optical inclusions in the medicament by utilizing at least one optical sensor.

8. The syringe pump of claim 4 wherein the flow sensor is integrated into an IV tube attached to the syringe and communicating with a patient.

9. The syringe pump of claim 1 wherein the pressure sensor is a component of the flow sensor.

10. The syringe pump of claim 1 wherein the flow error is detected by comparing flow to the acceptable flow range being a function of whether the motor drive is moving the plunger portion.

* * * * *